United States Patent
Kemény et al.

(10) Patent No.: US 9,839,595 B2
(45) Date of Patent: Dec. 12, 2017

(54) COMPOSITION FOR INCREASING OF THE EFFECTIVENESS OF UV-B THERAPY, PROCESS FOR THE PREPARATION THEREOF, AND ITS USE

(71) Applicant: GLOBALDERM KOZMETOLÓGIAI KORLÁTOLT FELELŐSSÉGŰ TÁRSASÁG, Szeged (HU)

(72) Inventors: Lajos Kemény, Szeged (HU); Piroska Révész, Szeged (HU); Erzsébet Csányi, Szeged (HU)

(73) Assignee: GD Photonics Kft., Szeged (HU)

( * ) Notice: Subject to any disclaimer, the term of this patent is extended or adjusted under 35 U.S.C. 154(b) by 0 days.

(21) Appl. No.: 14/760,375

(22) PCT Filed: Dec. 19, 2013

(86) PCT No.: PCT/HU2013/000130
§ 371 (c)(1),
(2) Date: Jul. 10, 2015

(87) PCT Pub. No.: WO2014/111737
PCT Pub. Date: Jul. 24, 2014

(65) Prior Publication Data
US 2015/0352026 A1   Dec. 10, 2015

(30) Foreign Application Priority Data
Jan. 17, 2013   (HU) ..................... 1300025

(51) Int. Cl.
| A61K 8/02 | (2006.01) |
| A61K 8/72 | (2006.01) |
| A61K 8/49 | (2006.01) |
| A61K 8/04 | (2006.01) |
| A61N 5/06 | (2006.01) |
| A61Q 19/00 | (2006.01) |
| A61K 8/67 | (2006.01) |
| A61K 8/73 | (2006.01) |
| A61Q 17/04 | (2006.01) |
| A61K 8/86 | (2006.01) |
| A61K 31/455 | (2006.01) |
| A61K 31/728 | (2006.01) |
| A61K 9/06 | (2006.01) |
| A61K 47/36 | (2006.01) |
| A61K 9/12 | (2006.01) |
| A61K 8/34 | (2006.01) |
| A61K 8/81 | (2006.01) |

(52) U.S. Cl.
CPC ........... *A61K 8/72* (2013.01); *A61K 8/042* (2013.01); *A61K 8/046* (2013.01); *A61K 8/345* (2013.01); *A61K 8/4926* (2013.01); *A61K 8/675* (2013.01); *A61K 8/735* (2013.01); *A61K 8/8147* (2013.01); *A61K 8/86* (2013.01); *A61K 9/06* (2013.01); *A61K 9/12* (2013.01); *A61K 31/455* (2013.01); *A61K 31/728* (2013.01); *A61K 47/36* (2013.01); *A61N 5/06* (2013.01); *A61Q 17/04* (2013.01); *A61Q 19/00* (2013.01); *A61K 2800/26* (2013.01); *A61K 2800/54* (2013.01); *A61K 2800/594* (2013.01); *A61K 2800/805* (2013.01); *A61N 2005/0661* (2013.01)

(58) Field of Classification Search
None
See application file for complete search history.

(56) References Cited

U.S. PATENT DOCUMENTS

| 5,489,279 | A | 2/1996 | Meserol |
| 5,501,849 | A | 3/1996 | Lee |
| 5,891,451 | A | 4/1999 | Guerrero et al. |
| 6,231,593 | B1 | 5/2001 | Meserol |
| 6,429,218 | B1 | 8/2002 | Scivoletto et al. |
| 2004/0120572 | A1 | 6/2004 | Luo et al. |
| 2004/0146539 | A1 | 6/2004 | Gupta |
| 2004/0180020 | A1* | 9/2004 | Manelski ........... A61K 8/31 424/70.12 |
| 2006/0178614 | A1 | 8/2006 | Nemati |
| 2007/0159592 | A1 | 7/2007 | Rylander et al. |
| 2007/0264345 | A1* | 11/2007 | Eros ........... A61K 9/0014 424/488 |
| 2008/0044494 | A1 | 2/2008 | Robinson et al. |
| 2010/0047360 | A1 | 2/2010 | Klaveness et al. |

FOREIGN PATENT DOCUMENTS

| WO | 2005/062938 A2 | 7/2005 |
| WO | 2005/120572 A1 | 12/2005 |

* cited by examiner

*Primary Examiner* — Susan Tran
(74) *Attorney, Agent, or Firm* — Jason D. Voight (57) ABSTRACT

A light-therapeutic composition is disclosed, which can modify the optical characteristics of the skin, thereby increase the effectiveness of the UV-B therapy. The composition according to the invention includes one or more material, which sets the minimum value of wavelength of the light transmitted, one or more material, which is suitable to modify the above-mentioned wavelength value, and increase the transmittance of the skin in a certain wavelength-range, furthermore, optionally an excipient. The composition according to the invention blocks the UV radiation in the wavelength ranging from 280 to 300 nm, and helps the incorporation of the UV radiation by the skin in the wavelength ranging from 310 to 320 nm.

12 Claims, 11 Drawing Sheets

Fig. 1. Penetration of ultraviolet B radiation into the skin

A: Without pre-treatment

B: After pre-treatment

Fig. 2. Spray formulation of the composition

Fig. 3. Gel formulation of the composition

Fig. 4. Macrogol 400

Fig. 5. Propylene glycol

Fig. 6. Carbopol 971P

Fig. 7. Carbopol Ultrez 10

Fig. 8. Carbopol 980 NF

Fig. 9. Zinc hyaluronate

Fig. 10. Glycerin

Fig. 11. Isopropyl myristate

Fig. 12. Migliol 810

Fig. 13. Macrogol 200

Fig. 14. Macrogol 300

Fig. 15. Macrogol 600

Fig. 16. Sodium hyaluronate

Fig. 17. Nicotinic acid

Fig. 18. Lactic acid

Fig. 19. Methenamine

Fig. 20. Transcutol

Fig. 21. Polyaminopropyl-biguanide (Cosmocil CQ)

Fig. 22. Optical transmittance spectra of the gel formulation of the composition in the ultraviolet range of wavelengths for different layer thicknesses

COMPOSITION FOR INCREASING OF THE EFFECTIVENESS OF UV-B THERAPY, PROCESS FOR THE PREPARATION THEREOF, AND ITS USE

BRIEF SUMMARY OF THE INVENTION

Subject matter of the invention is a light-therapeutic composition, which can modify the optical characteristics of the skin, thereby increase the effectiveness of ultraviolet B light-therapy. The composition according to the invention comprises one or more materials, which set the minimum value of wavelength of the light transmitted, one or more materials, which are suitable to modify the value of wavelength set by the said one or more materials and increase the transmittance of the skin in a certain wavelengths range, and optionally an excipient. The composition according to the invention blocks the ultraviolet radiation in the wavelength ranging from 280 to 300 nm, and facilitates the transmission of the ultraviolet radiation into the skin in the wavelength ranging from 310 to 320 nm.

BACKGROUND OF THE INVENTION

Ultraviolet light has been successfully utilized in the treatment of allergic and autoimmune skin diseases for decades as it prevents the development of antigen induced cellular immune response and induces immune tolerance. (Streilein J W, Bergstresser P R: Genetic basis of ultraviolet-B on contact hypersensitivity. Immunogenetics 27: 252-258, 1988). The immunosuppressive effect of ultraviolet radiation can mainly be associated with the inhibition of antigen presentation and the induction of apoptosis in T cells. Both ultraviolet B light-therapy (280-320 nm) and ultraviolet A irradiation (320-400 nm) following a pre-treatment with the photosensitizing agent psoralen can successfully inhibit the immunological processes in the skin.

Several light-therapy devices are available for treatment of certain dermatological disorders (e.g. psoriasis, atopic dermatitis) by therapeutic ultraviolet irradiation of the skin. Previously, for purposes of ultraviolet light therapy, devices emitting broad-band ultraviolet B (BB-UVB) radiation were used. Recently, the more effective narrow-band ultraviolet B (NB-UVB) systems have become common as they minimize the delivery of ultraviolet B radiation of less than 300 nm wavelength, which is responsible for inflammation but mainly lacks therapeutic effect. (Degitz K, Messer G, Plewig G, Röcken M: Schmalspektrum-UVB 311 nm versus Breitspektrum-UVB. Neue Entwicklungen in der Phototherapie. Hautarzt 49: 795-806, 1998). Our studies performed in psoriatic patients have demonstrated that xenon chloride excimer laser emitting ultraviolet B light of 308 nm wavelength provides an even greater therapeutic effect. (Bónis B, Kemény L, Dobozy A, Bor Zs, Szabó G, Ignácz F: 308 nm UVB excimer laser for psoriasis. The Lancet 35: 1522, 1997; Kemény L, Bónis B, Dobozy A, Bor Z, Szabo G, Ignacz F: 308-nm excimer laser therapy for psoriasis. Arch Dermatol. 137: 95-96, 2001; Novak Z, Bónis B, Baltás E, Ocsovszki I, Ignácz F, Dobozy A, Kemény L: The xenon chloride ultraviolet B laser is more effective in treating psoriasis and in inducing T cell apoptosis than narrow-band ultraviolet B. J Photochem Photobiol B 67:32-38, 2002).

Apart from the type of the light therapy system, the effectiveness of the treatment is further influenced by the reflection of the ultraviolet radiation from the skin surface. On a dry and scaly desquamating skin surface, the reflection of ultraviolet light is increased. As a result, only a lower proportion of the radiation will penetrate the skin and the therapeutic effect will be decreased. The problem is under active investigation and a number of different mechanical devices and methods have been and are still being developed to modify the optical properties of biological tissues (Rylander Cristopher G. et al.: US20070159592 patent application).

However, there are not only mechanical but also chemical solutions available to address the problem. Paraffin oil is often administered to the skin surface prior to ultraviolet irradiation to prevent its reflection and therefore enhance the effectiveness of light therapy. Paraffin oil itself does not absorb ultraviolet radiation but reduces skin desquamation which are together responsible for its beneficial effect. In the clinical setting, however, pre-treatment with paraffin oil is only rarely performed due to the cosmetically not acceptable nature of the substance, which stains clothing and causes patients to have difficulties with getting dressed after the treatment. On the other hand, other compositions, which are cosmetically favourable, often absorb ultraviolet light and therefore decrease the effectiveness of light therapy. Application of higher doses of ultraviolet B radiation, however, may lead to adverse effects.

Optical enhancement of skin transmittance may result in greater effectiveness of light therapy, but it has been proven that for therapeutic purposes, the most effective part of ultraviolet B spectrum is the range between 310 and 320 nm wavelength. Ultraviolet B radiation ranging from 280 to 320 nm wavelength has only a lower therapeutic effect while causing more severe skin inflammation. Therefore, an effective method is required to facilitate the penetration of ultraviolet B radiation of appropriate wavelength into the skin by reducing reflection from the skin surface, as well as to prevent the penetration of shorter wavelength components of ultraviolet B spectrum, therefore, reducing skin inflammation.

STATE OF THE ART

Subject matters of US2006178614 patent application are a method, composition, and apparatus for enhancing the in vivo optical transparency of biological tissues during radiotherapy. The composition exerts its effect by a penetration-enhancing agent and a clarification agent. The clarification agent is topically applied around the target tissue, whereby surrounding tissue will be prevented from damage while treating the target surface. The composition according to the said patent application is not suitable for the utilization in ultraviolet B light therapy and does not exhibit the dual effect enabling the penetration of the therapeutically effective range and the filtering of the harmful part of ultraviolet B radiation.

Subject matters of US2007159592 patent application are systems, devices, and methods for non-invasively modifying, maintaining, or controlling the optical properties of local tissues for diagnostic and therapeutic purposes. The method further comprises controlling the temperature of the tissue illuminated. The method applies a mechanical device to modify the optical properties of the skin.

Subject matter of U.S. Pat. No. 5,489,279 patent application is a method of applying photodynamic therapy to dermal lesions including the utilization of monochromatic red light of 635 nm wavelength. The method includes the use of a 5-ALA based hydrogel to enhance the optical transparency of the upper layer of the skin. Subject matter of this patent application refers not to the ultraviolet B spectrum.

Subject matters of WO2005062938 international patent application are compositions comprising polyurethane prepolymers, methods for producing such compositions and for optical clearing of skin, and use of these methods and compositions for modifying the effect of light-based therapies. The compositions and methods are effective by reducing surface scattering of and enhancing light penetration into the skin. This patent application does not specify the therapeutically relevant range of ultraviolet spectrum and does not exhibit the dual effect enabling the penetration of the therapeutically effective range and the filtering of the harmful part of ultraviolet B radiation.

Subject matter of US2008044494 patent application is a skin nourishing composition comprising silicone elastomers. This patent application indicates the regulation of mammalian skin condition as main function of the composition. Though the composition is suitable for preventing the harmful effects of ultraviolet radiation, it is not suitable for enhancing the effects of ultraviolet B light therapy and filtering of specific range of ultraviolet B spectrum.

Subject matter of U.S. Pat. No. 6,231,593 patent application is an apparatus for photodynamic therapy. This patent application indicates the application of a so-called hydrogel to hydrate and soften the upper layer of the skin to enhance its optical transparency for light and chemical transparency for pharmaceuticals. The hydrogel according to this patent application is not suitable for filtering of the harmful range of ultraviolet B spectrum.

Subject matter of EP0702568 European patent application is an emollient composition for radiotherapy of certain skin diseases, which absorbs only an insignificant amount of the applied ultraviolet radiation. The composition according to this patent application is suitable for the utilization in ultraviolet B light therapy, but does not exhibit the dual effect enabling the penetration of the therapeutically effective range and the filtering of the harmful part of ultraviolet B radiation.

It is therefore obvious that according to the state of the art, several mechanical and chemical solutions have been developed to improve the effectiveness of various light-therapeutic modalities including ultraviolet B light therapy by enhancing the penetration of radiation through the skin, but none of them is suitable for preventing the penetration of the harmful components of the incident radiation. Therefore, effective compositions improving the effectiveness of ultraviolet light therapy are needed to prevent inflammatory reactions arising as adverse effects of the therapy and thereby to overcome shortcomings and limitations of the state of the art. In order to meet the above demands the inventors have been conducted systematic research and development resulting in the accomplishment of this invention described in details below.

DETAILED DESCRIPTION OF THE INVENTION

Definitions

The term "excipient" refers in this description to an agent, which allows the light to penetrate into the skin in a wavelength range above the value relevant for the use of this invention. Such excipients include, but are not restricted to the followings: triethanolamine, Microkill COS, and distilled water. Selection of said excipient(s) and determination of its/their applicable quantity/quantities is concerned the common general knowledge of the skilled person and can be made without undue burden.

The term "dosage form" refers in this description to the type of the formulation of the composition, which is not particularly restricted, provided that the given dosage form is suitable for the appropriate delivery of the composition according to the invention onto the target skin surface. Such applicable dosage forms include, but are not restricted to the followings: solution, gel, ointment, cream, foam, spray, emulsion, and tonic. Selection of said dose formulation(s) is concerned the common general knowledge of the skilled person and can be made without undue burden.

Underlying Observations

During their systematic experimental work aiming at the development of this invention, inventors were surprised to see that, in contrast to the current state of the art, their compositions exhibit a dual effect by blocking ultraviolet B radiation of 280-300 nm wavelength responsible for skin inflammation while facilitating the skin penetration of 310-320 nm range of the ultraviolet B spectrum providing therapeutic effects. Said compositions are therefore able to prevent skin inflammation caused by ultraviolet B radiation of shorter wavelengths and to improve the effectiveness of ultraviolet B light therapy.

Detailed Description of the Invention

Subject matter of the present invention is a composition can modify the optical transmittance of the skin within the ultraviolet spectrum. Said composition comprises one or more materials, which set the minimum wavelength of the light transmitted; one or more materials, which are suitable to modify the value of wavelength set by the said materials and increase the optical transmittance of the skin in a defined wavelength range; and optionally excipient(s).

Figure 1:
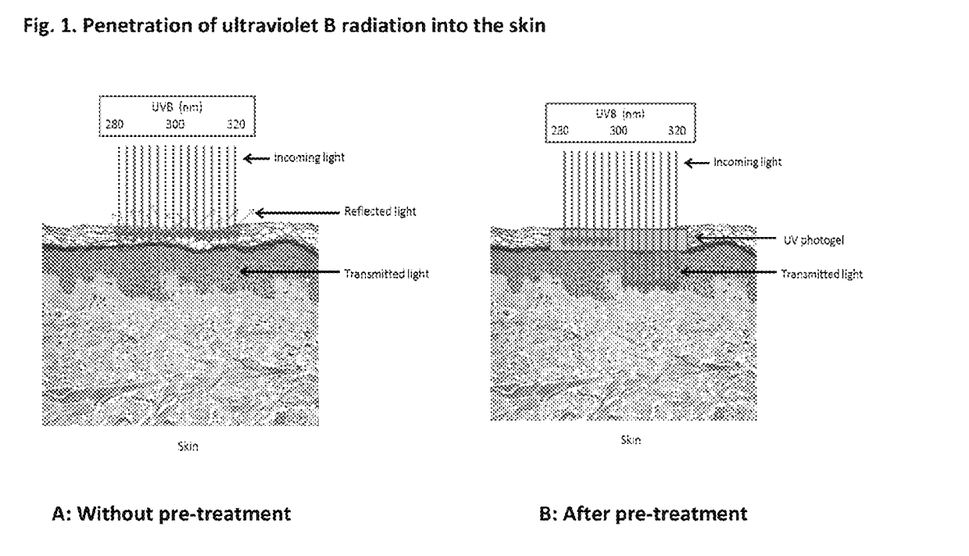
FIG. 1 shows the penetration of ultraviolet B radiation into the skin without pre-treatment and after pre-treatment with the composition according to the present invention.

A specific feature of the present invention is the ability to block the ultraviolet radiation in the range of 280-300 nm wavelength and to facilitate its penetration into the skin in the range of 310-320 nm wavelength. Specific filtering of short-wave ultraviolet B rays responsible for skin inflammation is carried out with facilitating the penetration of the therapeutically useful range of ultraviolet B radiation (310-320 nm) into the skin by inhibiting the reflection of ultraviolet B rays from the skin surface by means of optical correction (FIG. 1).

Therefore, the choice of the applicable material according to the invention is not particularly restricted, provided that the agent is able to set the wavelength of the transmitted light to the desired value. In this particular case the minimum wavelength is between 280-300 nm. Such materials include, but are not restricted to: Carbopol Ultrez 10, Carbopol 980 NF, zinc hyaluronate, glycerin, isopropyl myristate, Migliol 810, Macrogol 200, Macrogol 300, Macrogol 600, Carbopol 971P, propylene glycol, and Macrogol 400. Selection of said agent(s) and determination of its/their applicable quantity/quantities is concerned the common general knowledge of the skilled person and can be made without undue burden.

As per above, the choice of the other applicable material according to the invention is not particularly restricted, provided that the component is able to modify and enhance the optical transmittance of the skin in the ultraviolet B spectrum above 300 nm, in particular in the wavelength range between 310-320 nm. Such materials include, but are not restricted to: lactic acid, methenamine, transcutol and/or polyaminopropyl biguanide, sodium hyaluronate, and nicotinic acid. Selection of said agent(s) and determination of its/their applicable quantity/quantities is concerned the common general knowledge of the skilled person and can be made without undue burden.

As per above, the choice of the applicable excipient according to the invention is not particularly restricted, provided that the excipient does not decrease the effectiveness of the composition according to the present invention, i.e. it transmits light in a particular range of wavelengths above the wavelength relevant for the application. Such excipients include, but are not restricted to the followings: triethanolamine, Microkill COS, and distilled water. Selection of said excipient(s) and determination of its/their applicable quantity/quantities is concerned the common general knowledge of the skilled person and can be made without undue burden.

As per above, the composition according to the present invention contains the following materials in the following concentrations:

| | |
|---|---|
| Propylene glycol | from 0.1 to 10 percent by mass (0.1-10 wt %) |
| Carbopol 971P | from 0.1 to 0.5 percent by mass (0.1-0.5 wt %) |
| Carbopol Ultrez 10 | from 0.1 to 5 percent by mass (0.1-5 wt %) |
| Carbopol 980 NF | from 0.1 to 5 percent by mass (0.1-5 wt %) |
| Zinc hyaluronate | from 0.01 to 3 percent by mass (0.01-3 wt %) |
| Glycerin | from 0.1 to 30 percent by mass (0.1-30 wt %) |
| Isopropyl myristate | from 1 to 10 percent by mass (1-10 wt %) |
| Migliol 810 | from 1 to 30 percent by mass (1-30 wt %) |
| Macrogol 200 | from 10 to 90 percent by mass (10-90 wt %) |
| Macrogol 300 | from 10 to 90 percent by mass (10-90 wt %) |
| Macrogol 400 | from 10 to 90 percent by mass (10-90 wt %) and/or |
| Macrogol 600 | from 10 to 90 percent by mass (10-90 wt %) |
| Sodium hyaluronate | from 0.1 to 0.7 percent by mass (0.1-0.7 wt %) |
| Nicotinic acid | from 0.01 to 1 percent by mass (0.01-1 wt %) |
| Lactic acid | from 0.1 to 5 percent by mass (0.1-5 wt %) |
| Methenamine | from 0.1 to 1 percent by mass (0.1-1 wt %) |
| Transcutol | from 0.1 to 10 percent by mass (0.1-10 wt %) |
| Polyaminopropyl biguanide | from 0.1 to 3 percent by mass (0.1-3 wt %) and/or |

The dosage form of the composition according to the present invention is not particularly restricted, provided that the given dosage form is suitable for the appropriate delivery of the said composition onto the target skin surface. Such applicable dosage forms include, but are not restricted to the followings: solution, gel, ointment, cream, foam, spray, emulsion, and tonic. Selection of said dose formulation(s) is concerned the common general knowledge of the skilled person and can be made without undue burden.

Subject matter of the invention includes the use of the said composition as therapeutic agent.

Subject matter of the invention further includes a method for the production of the said composition, wherein the accordingly selected components are contacted with each other in subsequent procedure steps known per se. For detailed description of each procedure step see "Examples".

Subject matter of the invention further includes the use of the said composition for enhancement of the effectiveness of ultraviolet light therapy. The said composition reduces skin reflectance (by correction of surface unevenness and improvement of optical transmittance), as well as inhibits the pro-inflammatory effects of light in a given range of wavelengths. By use of the composition the specific wavelength range of ultraviolet B radiation, which is responsible for adverse effects and unnecessary for therapeutic purposes (shorter wavelength components), is filtered. These above effects are achieved not by means of pharmaceutical effect but only by means of optical correction.

EXAMPLES

In this section, our invention will be described through examples both for implementation and efficacy, with reference to figures listed and attached below.

The goal of the inventors was to develop such compositions, which do not transmit light with a wavelength shorter than 290-300 nm but feature a markedly higher transmittance for radiation with a wavelength above this value. Dermal application required the constitution of a composition suitable for patients' use. In addition to therapeutic goals, the primary intention of the inventors was to create a non-greasy, non-shiny composition, which is well tolerated by patients.

Figure 17:
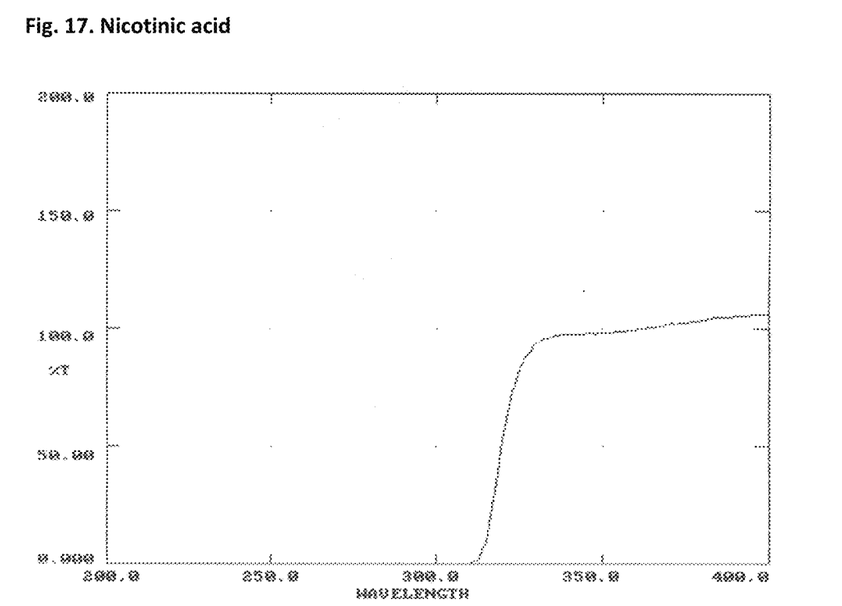
FIG. 17 shows optical transmittance spectrum of nicotinic acid.
Figure 18:
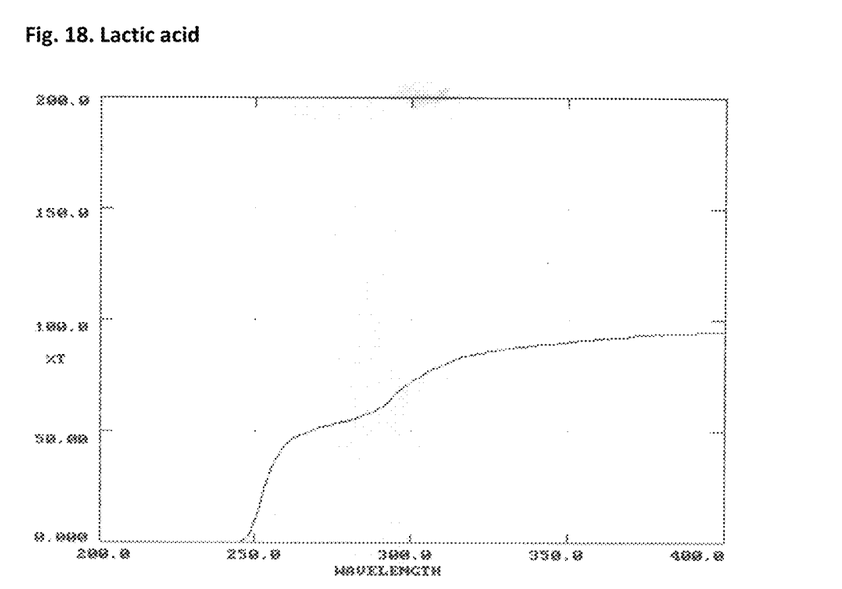
FIG. 18 shows optical transmittance spectrum of lactic acid.
Figure 19:
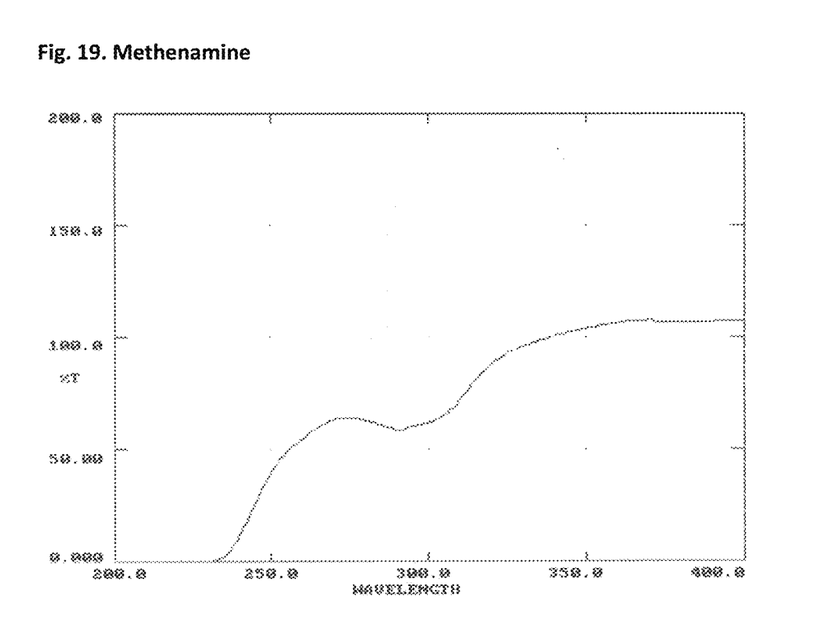
FIG. 19 shows optical transmittance spectrum of methenamine.
Figure 20:
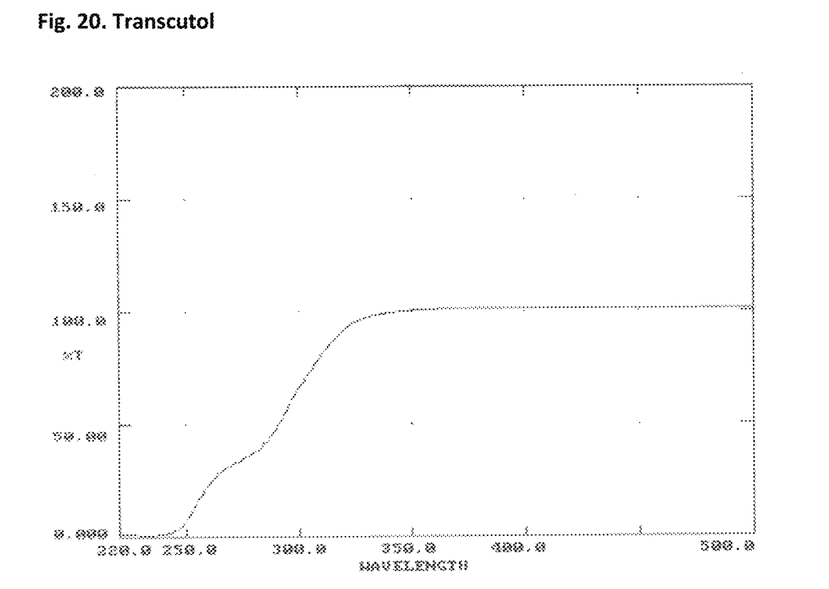
FIG. 20 shows optical transmittance spectrum of transcutol.
Figure 21:
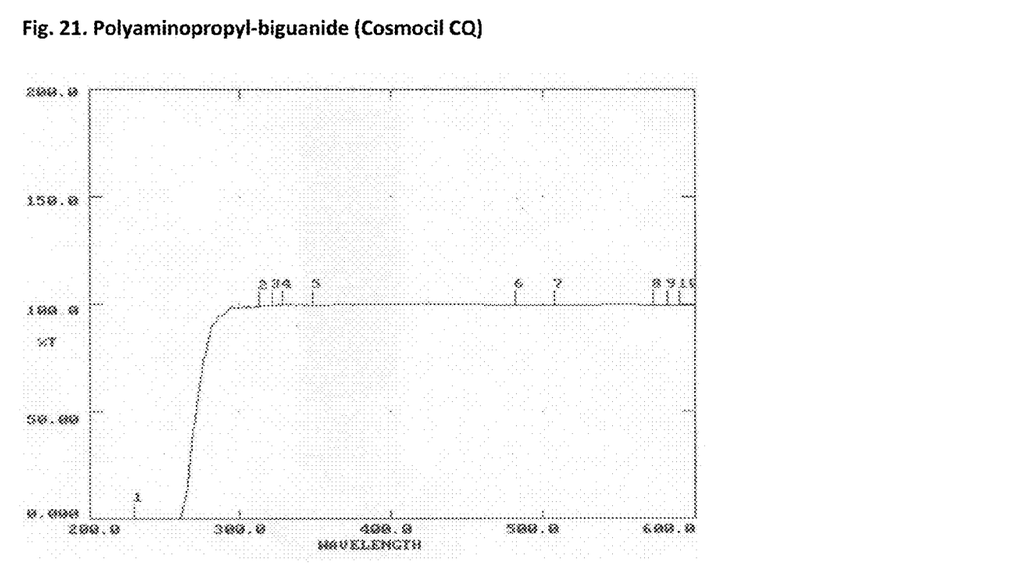
FIG. 21 shows optical transmittance spectrum of polyaminopropyl biguanide (Cosmocil CQ).

After measuring in vivo transmission of several agents inventors found that Macrogol 400 (FIG. 4) and sodium hyaluronate/Carbopol (FIG. 3) exhibit almost 100% transmission in the therapeutic wavelength range. Furthermore, a sharp decrease of transmittance was detectable around 300 nm wavelength and it fell to zero below this value. For nicotinic acid this effect is more pronounced (FIG. 17).

I. Composition of Samples Prepared for Clinical Trials

From among the numerous compositions tested, two samples have been selected for further development and in-depth clinical investigation.

Composition in Spray Form

Components of the sample:

| | |
|---|---|
| Nicotinic acid | 0.0405 g |
| Macrogol 400 (PEG 400) ad | 100.0 g |

Composition in Gel Form

Components of the sample:

| | |
|---|---|
| Sodium hyaluronate 1% aqueous gel | 20.0 g |
| Carbopol 971P 1% aqueous gel | 13.8 g |
| Propylene glycol | 10.0 g |
| Triethanolamine | 0.10 g |
| Microkill COS | 1.0 g |
| Distilled water ad | 100.0 g |

For the spray formulation, nicotinic acid was dissolved in Macrogol 400 at room temperature. For the gel formulation, first Microkill COS was mixed with propylene glycol, and both hydrogels, i.e. with sodium hyaluronate 1% aqueous gel, and Carbopol 971P 1% aqueous gel, respectively, and finally distilled water was added up to 100 grams.

Figure 2:
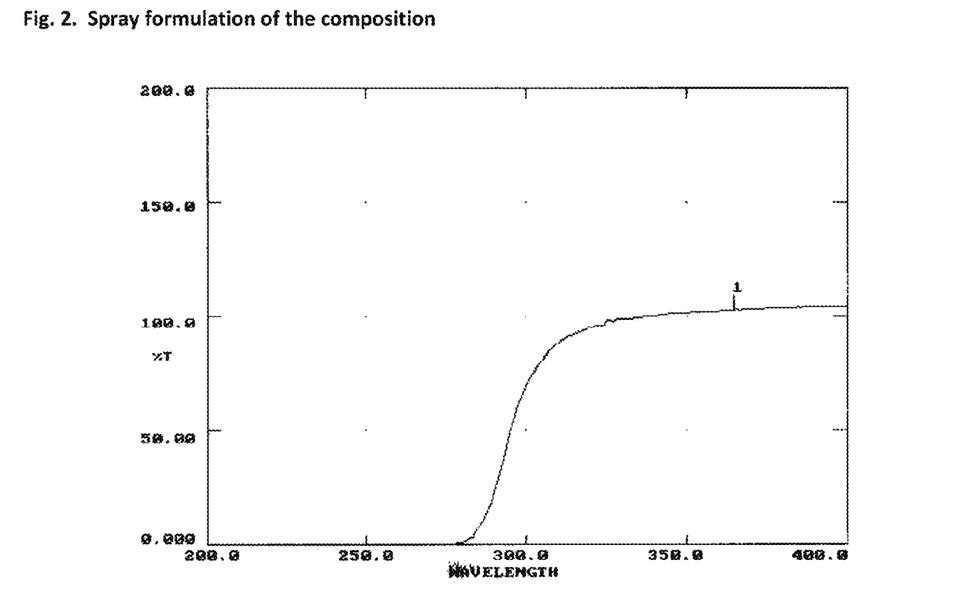
FIG. 2 shows optical transmittance spectrum of the spray formulation of the composition according to the present invention.
Figure 3:
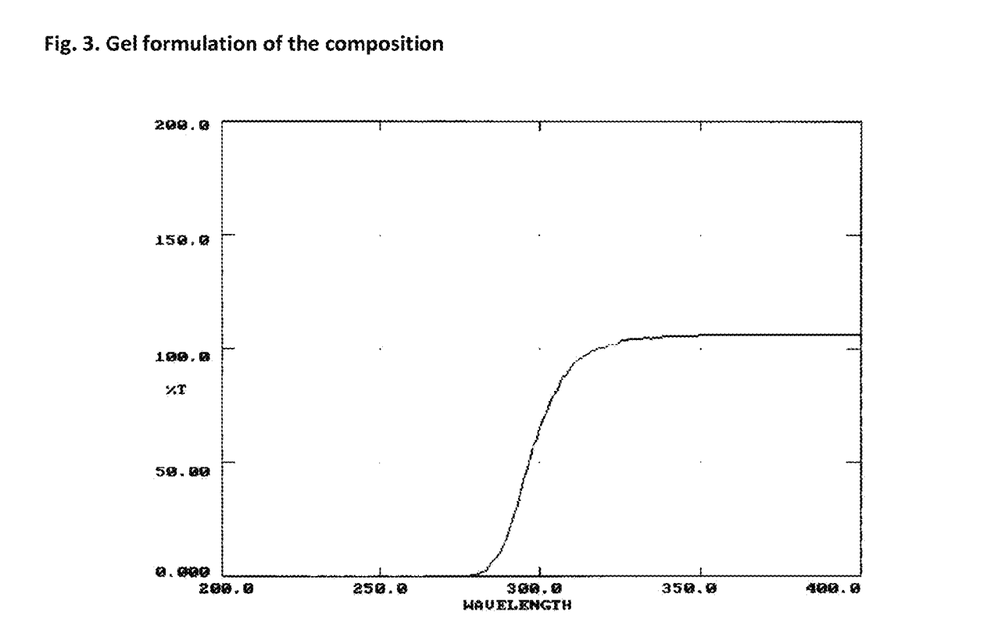
FIG. 3 shows optical transmittance spectrum of the gel formulation of the composition according to the present invention.
Figure 4:
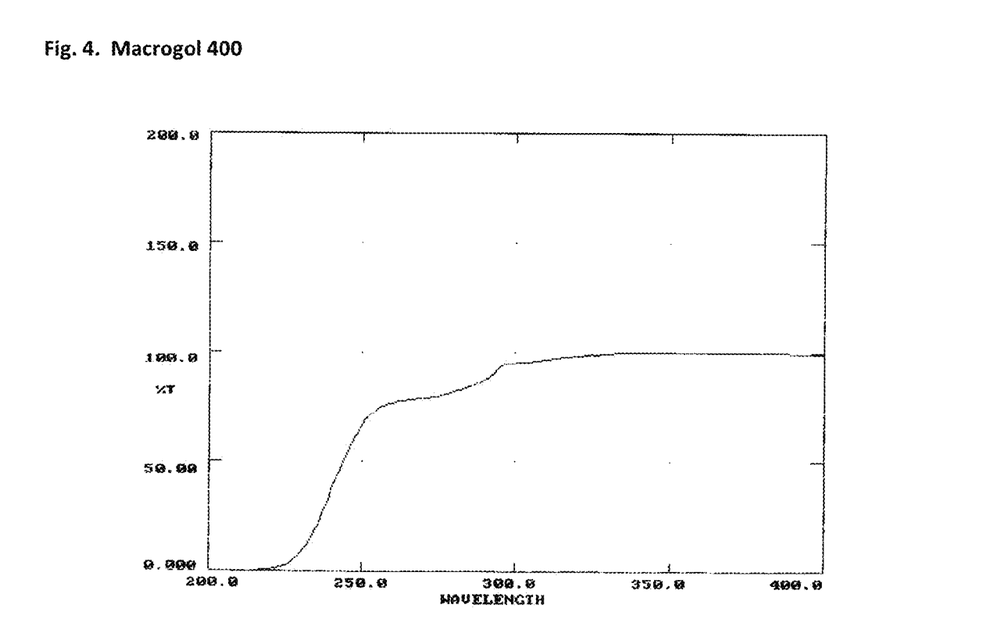
FIG. 4 shows optical transmittance spectrum of Macrogol 400 (PEG 400).
Figure 5:
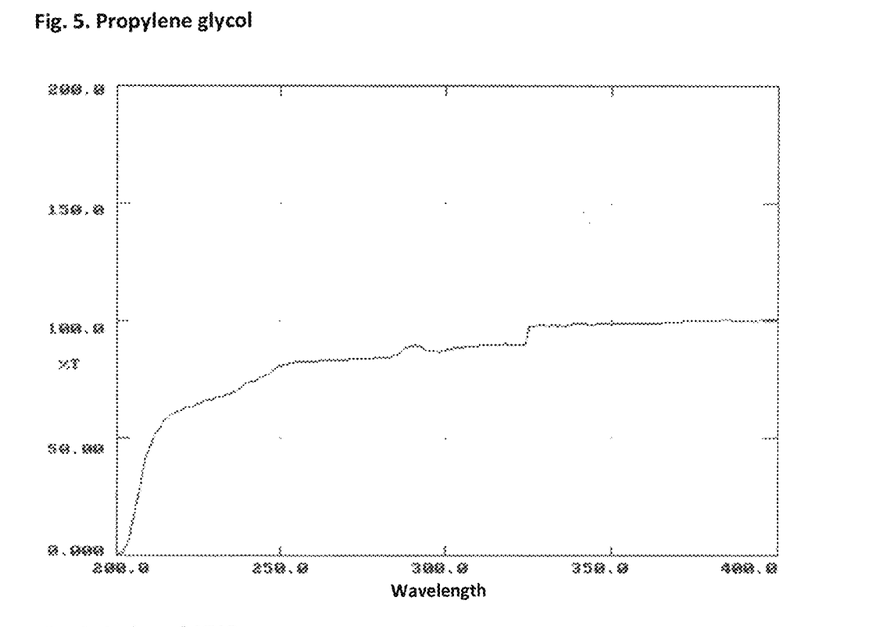
FIG. 5 shows optical transmittance spectrum of propylene glycol.
Figure 6:
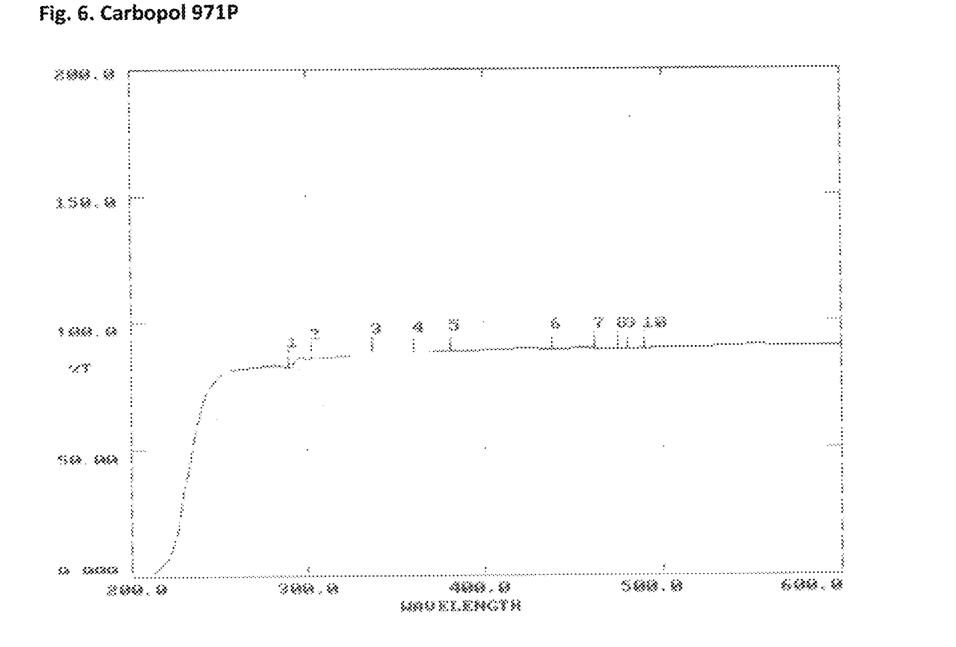
FIG. 6 shows optical transmittance spectrum of Carbopol 971P.
Figure 7:
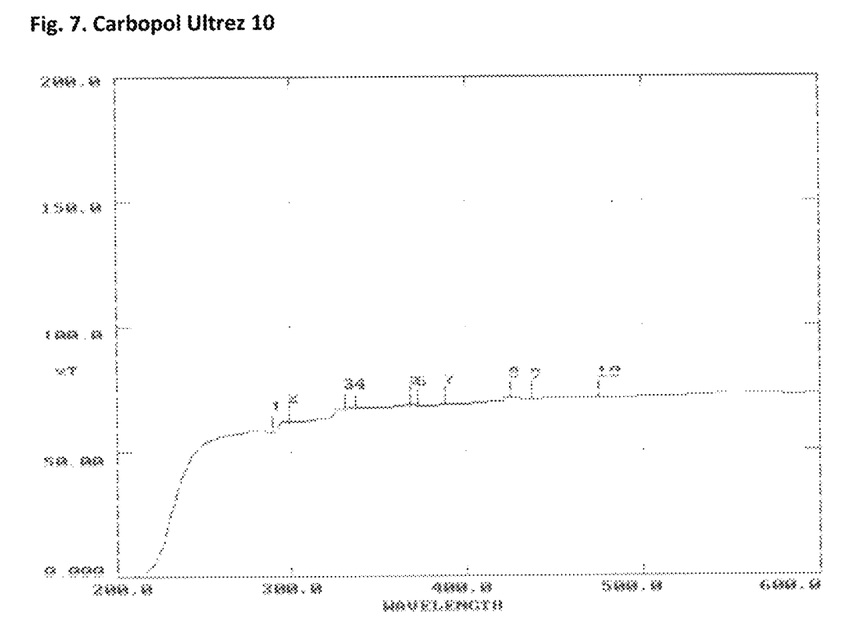
FIG. 7 shows optical transmittance spectrum of Carbopol Ultrez 10.
Figure 8:
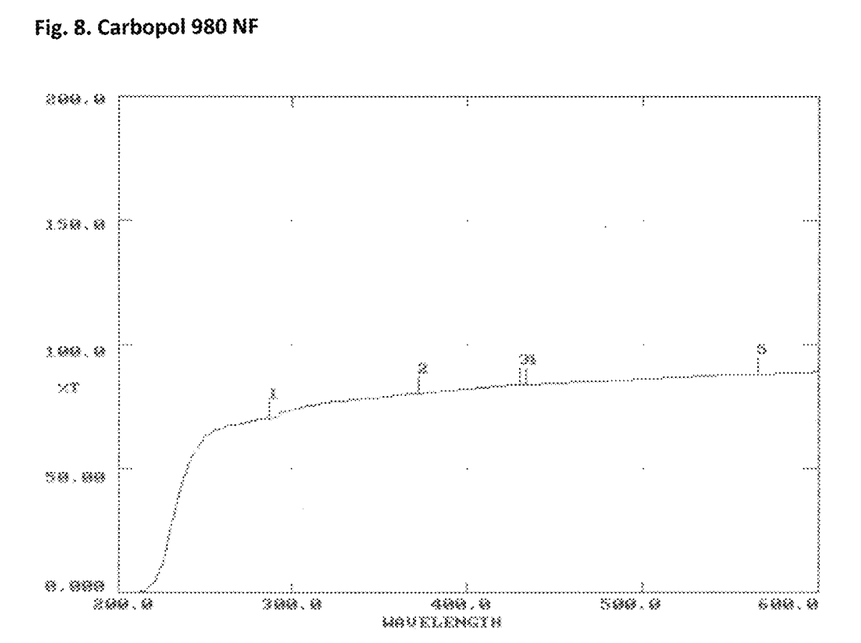
FIG. 8 shows optical transmittance spectrum of Carbopol 980 NF.
Figure 9:
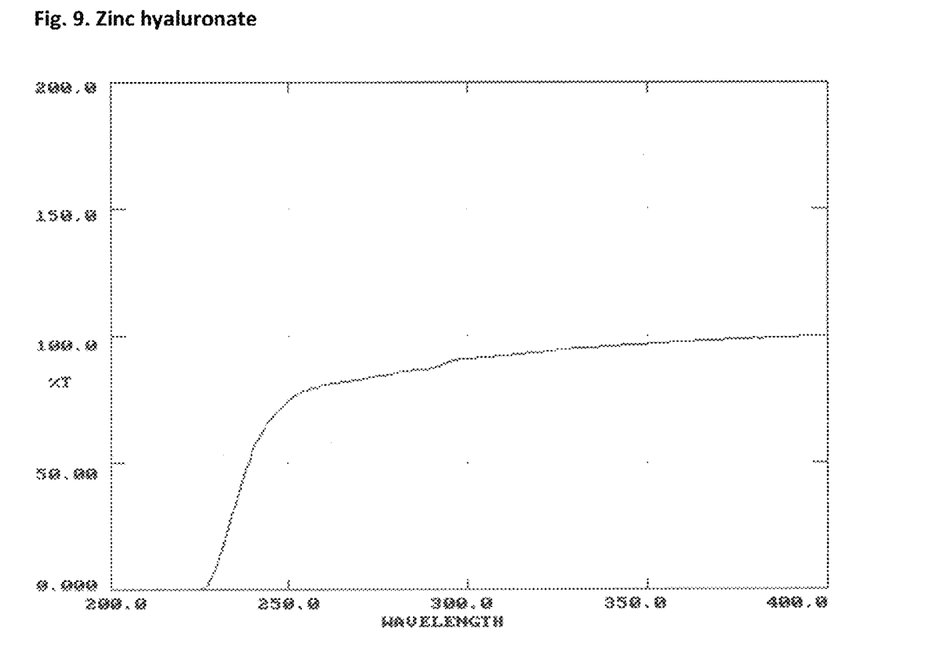
FIG. 9 shows optical transmittance spectrum of zinc hyaluronate.
Figure 10:
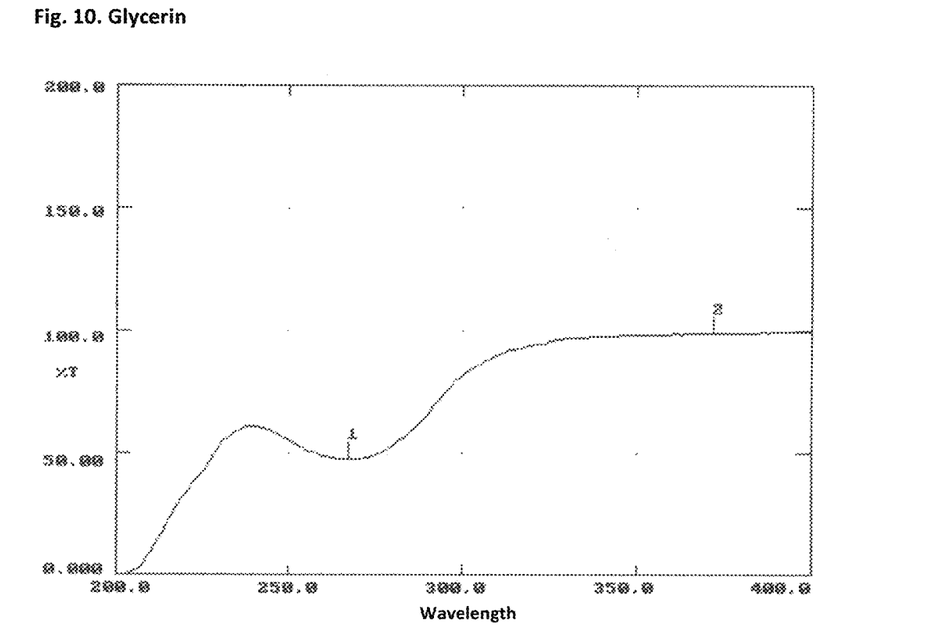
FIG. 10 shows optical transmittance spectrum of glycerin.
Figure 11:
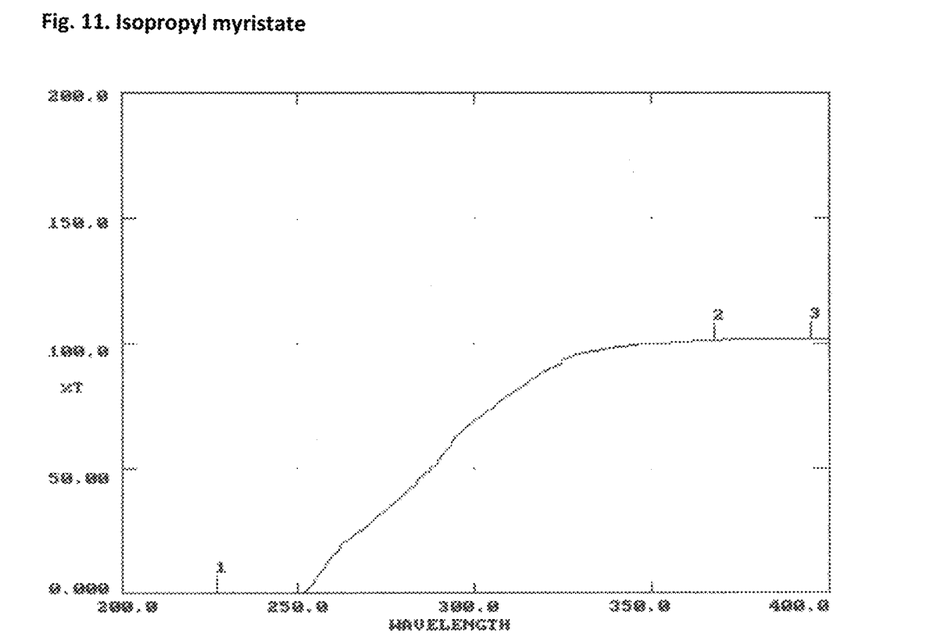
FIG. 11 shows optical transmittance spectrum of isopropyl myristate.
Figure 12:
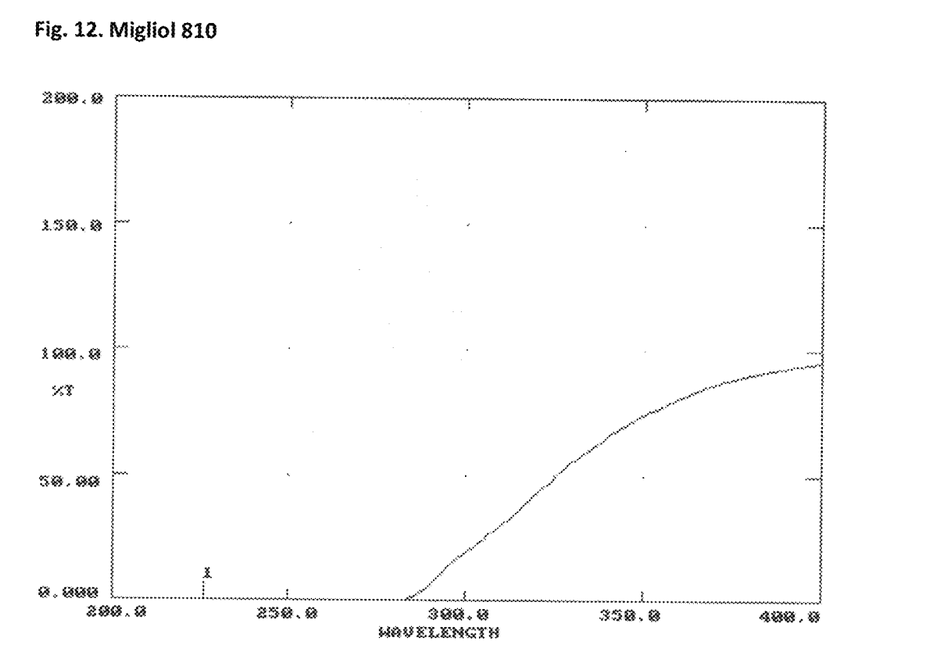
FIG. 12 shows optical transmittance spectrum of Migliol 810.
Figure 13:
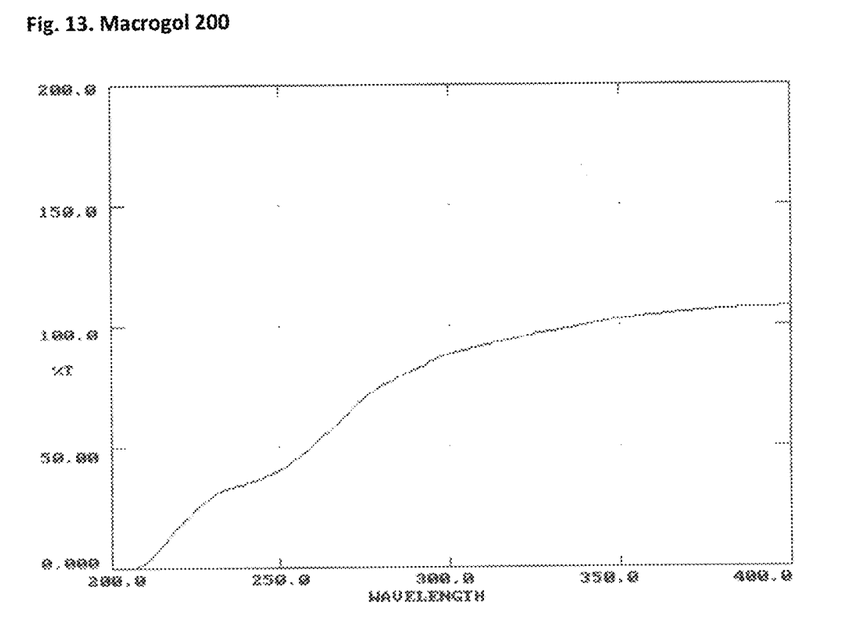
FIG. 13 shows optical transmittance spectrum of Macrogol 200.
Figure 14:
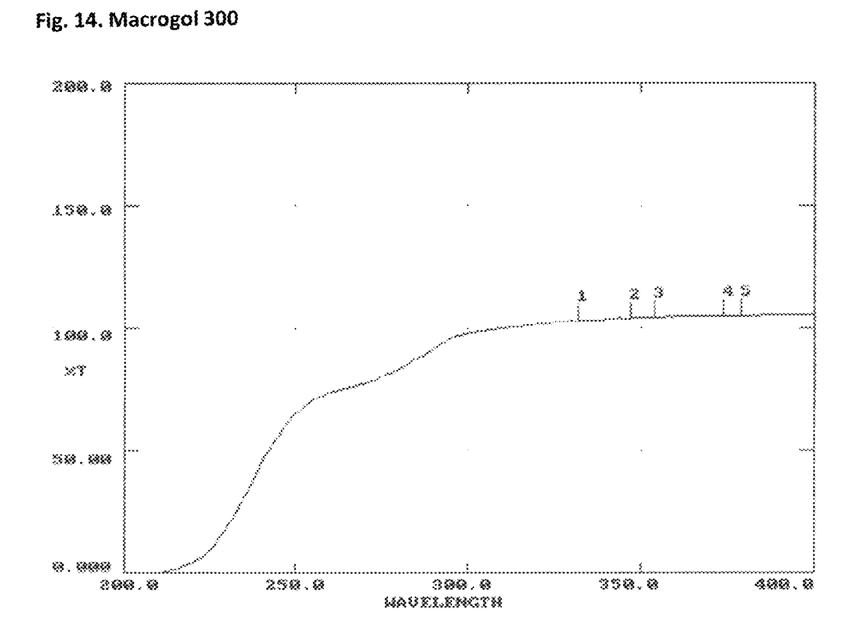
FIG. 14 shows optical transmittance spectrum of Macrogol 300.
Figure 15:
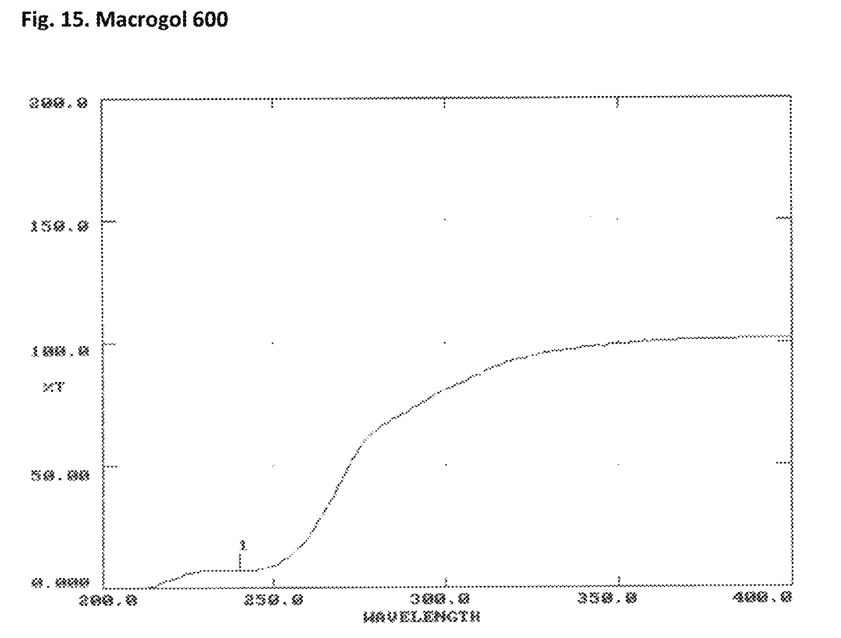
FIG. 15 shows optical transmittance spectrum of Macrogol 600.
Figure 16:
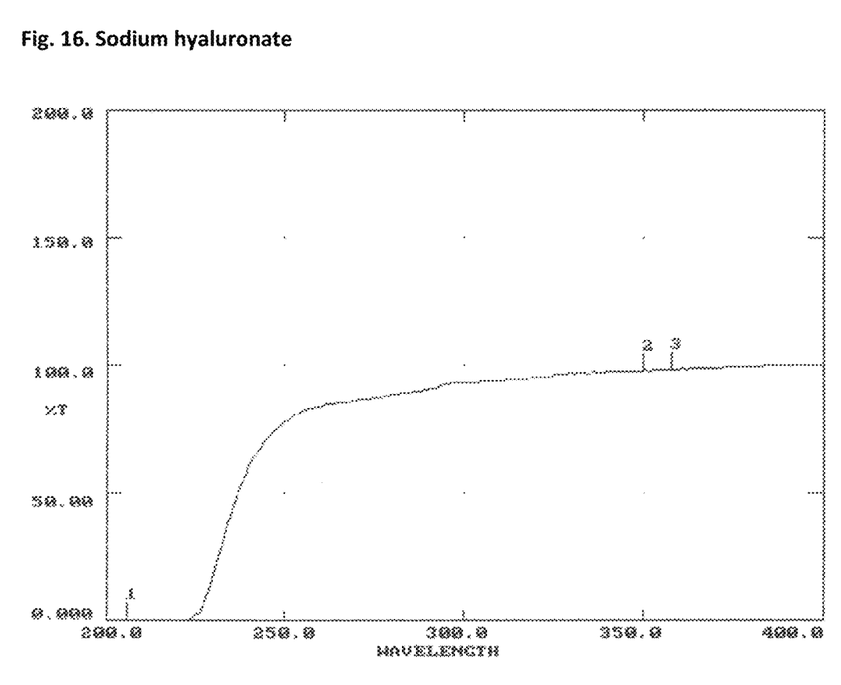
FIG. 16 shows optical transmittance spectrum of sodium hyaluronate.

Compositions suitable for therapeutic purposes were selected by the measurement of optical transmittance. Measurements were performed using a Helios a spectrophotometer in the wavelength range of 200-600 nm. FIGS. 4 and 2 show optical transmittance spectra of Macrogol 400 and the spray formulation of the composition, respectively. FIG. 3 illustrates the optical transmittance spectrum of the gel formulation of the composition.

II. Clinically Tested Samples

Initial In Vitro Tests

Figure 22:
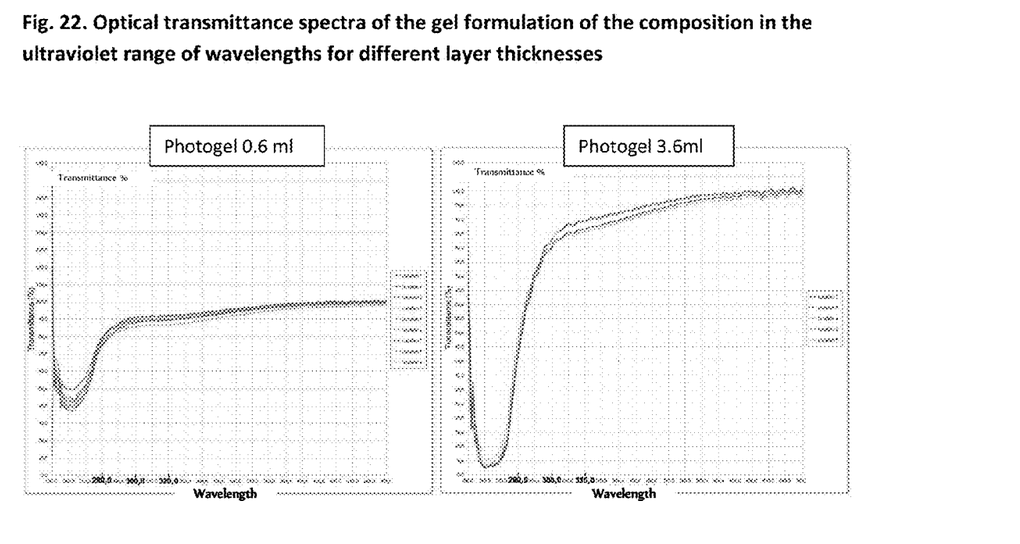
FIG. 22 shows ultraviolet transmittance spectra of 0.6 ml and 3.6 ml volumes of the spray formulation of the composition, respectively, measured by Lab sphere UV Transmittance Analyzer. Layer thickness was 0.24 mm and 1.44 mm, respectively (evenly spread on a polymethyl methacrylate [PMMA] disc of 50×50 mm) Wavelength range: 250-450 nm. Measuring points (9) and points determined by template (5).

In vitro tests were performed in accordance with the COLIPA SPF test method. Above 300 nm wavelength, the transmittance was almost 100%, while a sharp decrease was observed below 300 nm (FIGS. 2, 3 and 22). In the case of lower wavelength the transmittance decreased with increasing thickness of the layer on the disc (FIG. 22).

Initial In Vivo Tests I

It was assessed whether the spray or gel formulation of the composition has any effect on the minimal erythema dose (MED) during ultraviolet light therapy in the therapeutic range of wavelengths. MED was determined on skin surfaces with and without pre-treatment. Light source for the experiments was a selective ultraviolet B phototherapy (SUP) lamp with the following properties: (292.5-335 nm), and a TH-1 Skintester (280-320 nm). During the test 50 mJ/cm$^2$-1000 mJ/cm$^2$ light was applied. At the given wavelength there was no significant difference in MED between untreated and pre-treated skin areas for either light source.

In the following in vivo SPF values were measured according to COLIPA standards (light source was an SPF Solar Simulator Model 16S 150W, Solar Light Co.). In the wide range of wavelengths defined above SPF was <2, which means that due to their selective transmittance properties shown in the ultraviolet B spectrum, both the solution and the gel formulations of the composition have different mechanism of action than a common sunscreen. In subjects with dry skin both the solution and the gel formulation of the composition facilitated the penetration of ultraviolet B radiation into the skin and MED values were therefore a bit higher than in subjects with normal or oily skin.

Study Participants 20 patients with chronic plaque psoriasis (15 males, 5 females) between 18 and 65 years of age (mean age: 47.6 years) were enrolled into the study. At baseline, mean body surface area (BSA) affected by psoriasis was 12.9%. Patients for whom ultraviolet B light therapy was contraindicated were excluded from the study. Four patients received oral acitretin (25 mg/day) and 18 patients were treated by narrow-band ultraviolet B light therapy. One patient was subject to XeCl excimer laser therapy and another patient received oral PUVA therapy.

Light Therapy

Light therapy was performed using a Waldmann UV5000 cabinet equipped with Waldmann F85/100W-UV01 tubes, a Waldmann UV7001K cabinet equipped with Waldmann F85/100W-PUVA tubes, and a Photomedex Xtrac 308 nm XeCl excimer laser, respectively.

Patients were randomized into 2 treatment groups. Pre-treatment prior to light therapy was accomplished with the solution formulation of the composition in 10 patients and with the gel formulation of the composition in the remaining 10 patients. In both groups left and right sides of the body were compared to each other. For each patient one or two symmetrical plaque pairs were identified as target lesions for assessment. Regarding all 20 patients enrolled into the study, altogether 40 plaque pairs were identified. Target plaques were located on the upper or lower extremities or on the chest. One side of the body was randomly assigned for pre-treatment with the solution or gel formulation of the composition, while the other side of the body was pre-treated with liquid paraffin. Patients were blinded for the pre-treatment protocol. Before pre-treatment all plaques were assessed for size, infiltration and the severity of erythema according to a scale with the following values: 0=none; 1=mild; 2=moderate; 3=severe; 4=very severe. Scores were then summarized. A blinded investigator, who was not familiar with the pre-treatment protocol, performed the clinical assessment of plaques at baseline and in every two weeks thereafter. Pre-treatment was conducted by a qualified nurse a few minutes before each light therapy session. The trial was completed when the score for a particular plaque became equal to zero. Patients received treatments 2 to 3 times a week. At the end of the light therapy period, patients were asked about their preference for pre-treatment type.

Statistical Analysis

For each plaque pair comparison between sides pre-treated with liquid paraffin and the solution or gel formulation was performed by Spearman's rank correlation test (SPSS 15.0 software).

Results

Composition in Spray Form

In the group randomized for pre-treatment with the solution formulation of the composition, the trial was completed in the case of 9 patients. One subject dropped out from the trial due to the rapid progression of psoriasis that required systemic therapy. Mean plaque severity score was 6.64 for the body side pre-treated with the solution and gel formulation of the composition as we intended to choose comparable plaques. However, it was uncertain whether there is a significant difference in the improvement (target plaque score) between the sides pre-treated with liquid paraffin and the solution formulation of the composition. Assessments were done at week 4 in two patients and at week 6 in eight patients. Table 1 shows mean PASI scores for body sides pre-treated with liquid paraffin and the solution formulation of the composition at weeks 0, 2, 4 and 8.

TABLE 1

| | Week 0 | | Week 2 | | Week 4 | | Week 6 | |
|---|---|---|---|---|---|---|---|---|
| | liquid paraffin | solution | liquid paraffin | solution | liquid paraffin | solution | liquid paraffin | solution |
| Plaque score | 6.65 ± 1.32 | 6.65 ± 1.32 | 4.76 ± 1.20 | 4.82 ± 1.18 | 4.00 ± 2.45 | 3.65 ± 2.64 | 1.38 ± 1.19 | 0.85 ± 0.80 |

As shown in Table 2, there is at least a moderately strong positive correlation between scores for plaques pre-treated with liquid paraffin and those for plaques pre-treated with the solution or the gel formulation and all values significantly differ from zero. Therefore, liquid paraffin and the solution formulation of the composition seem to be interchangeable with each other.

TABLE 2

| | Week 0 Spearman's R | Week 2 Spearman's R | Week 4 Spearman's R | Week 6 Spearman's R |
|---|---|---|---|---|
| Erythema | 1.000 | 1.000 | 0.882 | 0.795 |
| Size | 1.000 | 0.835 | 1.000 | 1.000 |
| Infiltration | 1.000 | 0.704 | 0.853 | 0.589 |
| Altogether | 1.000 | 0.706 | 0.932 | 0.657 |

Composition in Gel Form

In the group assigned for pre-treatment with the gel formulation of the composition, the trial was completed in the case of all 10 patients. Mean plaque severity score was 6.91 for the body side pre-treated with the gel formulation of the composition and 6.83 for the body side pre-treated with liquid paraffin. Similarly to patients in the solution pre-treatment group, we selected target plaques suitable for comparison. However, it was uncertain whether there is a significant difference in the improvement (target plaque score) between sides pre-treated with liquid paraffin and the gel formulation of the composition. Assessments were done at week 4 in one patient, at week 6 in six patients and at week 8 in three patients. Table 3 shows mean PASI scores for body sides pre-treated with liquid paraffin and the gel formulation of the composition at weeks 0, 2, 4 and 8.

TABLE 3

| | Week 0 | | Week 2 | | Week 4 | | Week 6 | | Week 8 | |
|---|---|---|---|---|---|---|---|---|---|---|
| | liquid paraffin | gel | liquid paraffin | gel | liquid paraffin | gel | liquid paraffin | gel | liquid paraffin | gel |
| plaque score | 6.83 ± 1.11 | 6.91 ± 1.12 | 4.35 ± 0.88 | 4.83 ± 1.11 | 2.70 ± 1.92 | 3.35 ± 1.90 | 1.52 ± 1.57 | 1.52 ± 1.63 | 1.77 ± 1.72 | 1.55 ± 1.59 |

TABLE 4

| | Week 0 Spearman's R* | Week 2 Spearman's R | Week 4 Spearman's R | Week 6 Spearman's R |
|---|---|---|---|---|
| Erythema | 1.000 | 0.942 | 0.937 | 0.961 |
| Size | 0.920 | 0.550 | 0.456 | 1.000 |
| Infiltration | 0.936 | 0.377 | 0.701 | 0.771 |
| Altogether | 0.903 | 0.620 | 0.770 | 0.946 |

*Spearman's rank correlation coefficient

Tolerability

After completing the treatments patients were asked about their preference for the pre-treatment, i.e. which pre-treatment regimen they found the least unpleasant. The question was as follows: "Which pre-treatment did you find to be cosmetically more acceptable? The pre-treatment on the left side or on the right side of your body?" During the study data were also collected on the patients' subjective attitude to the pre-treatment. According to their reports, patients did not experience any adverse effects. Preference rates in the different groups were 7:2 (solution vs. liquid paraffin; 1 patient reported no difference between sides) and 9:1 (gel vs. liquid paraffin), respectively.

Safety

One subject dropped out from the trial due to the rapid progression of psoriasis that required systemic therapy. However, relation between aggravation of psoriasis and the trial was improbable. No adverse events were reported either in the solution or in the gel group.

Initial In Vivo Tests II

In our trial conducted in August 2011, 60 patients suffering from chronic plaque psoriasis were enrolled. Patients were treated by heliotherapy applying a common sunscreen with SPF 30 on symptom-free skin and the gel formulation of the composition on psoriatic plaques, immediately before sunbathing. The two-part study kit included therefore a common sunscreen with SPF 30 and the gel formulation of the composition.

As shown in Table 4, there is at least a moderately strong positive correlation between scores for plaques pre-treated with liquid paraffin and those for plaques pre-treated with the solution or the gel formulation and all values significantly differ from zero. Therefore, liquid paraffin and the solution formulation of the composition seem to be interchangeable with each other.

Depending on the number of days with sunshine, patients received the study treatment 4 to 5 times a week, for 4 weeks.

From among the 60 patients enrolled into the study, psoriatic symptoms were improved by >90% in 38 subjects, while 75-90% improvement were detected in 16 patients and 50-75% improvement in 6 patients, respectively. Worsening of psoriatic plaques or sunburn on symptom-free skin was not occurred in any of the patients. Patient found the administration of the two different compositions (one for the symptom-free skin surface and one for the psoriatic plaques) convenient and comfortable.

Results led to conclude that the combination treatment scheme, i.e. pre-treatment of psoriatic lesions with the gel formulation of the composition and the application of a common sunscreen on the symptom-free skin at the same time is a favourable regimen for heliotherapy.

INDUSTRIAL APPLICABILITY

Favourable effects of ultraviolet B radiation are utilized in the treatment of several dermatological disorders. However, due to certain physiological and pathophysiological features of the psoriatic skin (disintegration of stratum corneum, parakeratosis) its upper layer is characterized by an increased reflection and scattering of incident light. Therefore, effectiveness of light therapy does not reach the desired level while higher doses of radiation may increase the risk of adverse effects. Optical enhancement of skin transmittance may result in higher effectiveness of light therapy but only a specific part of the ultraviolet B spectrum is suitable for therapeutic purposes. Ultraviolet B radiation ranging from 280 to 320 nm wavelength has only a lower therapeutic effect but causes more severe skin inflammation while the spectral range between 310-320 nm demonstrates higher therapeutic effectiveness and a reduced pro-inflammatory potential.

The advantage of the present invention is thus, on the one hand, to facilitate the penetration of the therapeutically effective part of the ultraviolet B radiation into the skin and, on the other hand, to protect against the unwanted ranges of ultraviolet B spectrum which enables to use higher doses of ultraviolet B radiation during light therapy. By means of the present invention the effectiveness of light therapy will be enhanced while harmful side effects avoided.

The composition according to the present invention is photostable, non-photosensitizing and does not absorb the therapeutically active spectrum of ultraviolet B radiation. Further advantage of the composition according to the present invention is that it is cosmetically acceptable for the treated subjects. All components of the composition according to the present invention are well-tolerated and safe and neither of them alone nor as a mixture render the skin oily or fatty or stain clothing.

The above properties enable the composition according to the present invention to amend heliotherapy with an effective protection against the harmful part of ultraviolet radiation in various skin disorders. Several psoriatic patients prefer natural sunlight as treatment. In order to avoid sunburn, appropriate sunscreen should be applied on normal uninvolved skin. Application of a sunscreen is, however, not recommended on psoriatic skin as it may block the penetration of light into the plaques. In addition, the scaly, hyperkeratotic surface of the lesions can also reflect light. Different compositions can reduce this negative effect. Several investigations have demonstrated that the various emollients exert a sun protective effect. Compositions developed by the inventors enable a proper pre-treatment before sunbathing as they have the appropriate transmission spectrum, filter unnecessary wavelengths of ultraviolet radiation and are cosmetically well tolerated.

The invention claimed is:
1. A composition for modulating the optical transmittance of the skin within the ultraviolet spectrum comprising
   a) one or more materials for setting a minimum value of wavelength of the light transmitted, wherein the one or more materials are selected from the group consisting of carbomer interpolymer type A, carbomer homopolymer type C, zinc-hyaluronate, glycerin, isopropyl myristate, caprylic/capric triglyceride, PEG 200, PEG 300, PEG 600, carbomer homopolymer type A, propylene glycol, and PEG 400;
   b) a material for modifying the value of wavelength set by the one or more materials according to a) and enhancing the optical transmittance of the skin in a given range of wavelengths, wherein the material is nicotinic acid; and
   c) an excipient, which allows the light to penetrate into the skin in a wavelength range above the value relevant for the use, where the excipient is selected from the group consisting of triethanolamine, a combination of phenoxyethanol, caprylyl glycol and chlorphenesin, and distilled water.

2. The composition according to claim 1, wherein the composition comprises one or more of the following components in the given quantities:

| | |
|---|---|
| Propylene glycol | from 0.1 to 10 percent by mass (0.1-10 wt %), |
| carbomer homopolymer type A | from 0.1 to 0.5 percent by mass (0.1-0.5 wt %), |
| carbomer interpolymer type A | from 0.1 to 5 percent by mass (0.1-5 wt %), |
| carbomer homopolymer type C | from 0.1 to 5 percent by mass (0.1-5 wt %), |
| Zinc hyaluronate | from 0.01 to 3 percent by mass (0.01-3 wt %), |
| Glycerin | from 0.1 to 30 percent by mass (0.1-30 wt %), |
| Isopropyl myristate | from 1 to 10 percent by mass (1-10 wt %), |
| caprylic/capric triglyceride | from 1 to 30 percent by mass (1-30 wt %), |
| PEG 200 | from 10 to 90 percent by mass (10-90 wt %), |
| PEG 300 | from 10 to 90 percent by mass (10-90 wt %) |
| PEG 400 | from 10 to 90 percent by mass (10-90 wt %), |
| PEG 600 | from 10 to 90 percent by mass (10-90 wt %), |
| Benzaldehyde | from 0.001 to 1 percent by mass (0.001-1 wt %) and/or |
| Nicotinic acid | from 0.01 to 1 percent by mass (0.01-1 wt %). |

3. The composition according to claim 1, wherein the composition blocks the ultraviolet radiation in the wavelength range of 280-300 nm and facilitates its transmission into the skin in a wavelength range of 310-320 nm.

4. The composition according to claim 1, wherein the dosage form of the composition is solution, gel, ointment, cream, foam, spray, emulsion, or tonic.

5. A composition for modulating the optical transmittance of the skin within the ultraviolet spectrum comprising
   a) a material for setting a minimum value of wavelength of the light transmitted, wherein the material is PEG 400;
   b) a material for modifying the value of wavelength set by the materials according to a) and enhancing the optical transmittance of the skin in a given range of wavelengths, wherein the material is nicotinic acid,
   wherein the composition comprises in an amount of from 0.01 to 0.10 gram nicotinic acid per 100 grams of the composition and PEG 400.

6. The composition according to claim 1, wherein the composition comprises carbomer homopolymer type A 1% aqueous gel in an amount of 10 to 50 grams, propylene glycol in an amount of 0.1 to 10 grams, triethanolamine in an amount of 0.1 to 0.5 gram, the combination of phenoxyethanol, caprylyl glycol and chlorphenesin in an amount of 1 to 5 grams per 100 grams of the composition and distilled water.

7. A method for enhancing the effectiveness of ultraviolet light therapy, said method comprising delivering to a target skin surface of a patient in need of such therapy a composition comprising a) one or more materials for setting a minimum value of wavelength of the light transmitted, wherein the one or more materials are selected from the group consisting of carbomer interpolymer type A, carbomer homopolymer type C, zinc-hyaluronate, glycerin, isopropyl myristate, caprylic/capric triglyceride, PEG 200, PEG 300, PEG 600, carbomer homopolymer type A, propylene glycol, and PEG 400;

b) a material for modifying the value of wavelength set by the one or more materials according to a) and enhancing the optical transmittance of the skin in a given range of wavelengths, wherein the material is nicotinic acid; and c) an excipient, which allows the light to penetrate into the skin in a wavelength range above the value relevant for the use, wherein the excipient is selected from the group consisting of triethanolamine, a combination of phenoxyethanol, caprylyl glycol and chlorphenesin, and distilled water and performing ultraviolet light therapy on said patient.

8. The composition according to claim 1, wherein the composition comprises in an amount of 0.0405 gram nicotinic acid per 100 grams of the composition and PEG 400.

9. The composition according to claim 1, wherein the composition comprises carbomer homopolymer type A 1% aqueous gel in an amount of 13.8 grams, propylene glycol in an amount of 10 grams, triethanolamine in an amount of 0.1 gram, and the combination of phenoxyethanol, caprylyl glycol and chlorphenesin in an amount of 1 gram per 100 grams of the composition and distilled water.

10. The method of claim 7, wherein the target skin surface comprises a psoriatic plaque.

11. The method of claim 10, further comprising applying a common sunscreen on symptom-free skin outside of the target skin surface.

12. The method of claim 7, wherein said composition comprises the combination of phenoxyethanol, caprylyl glycol and chlorphenesin.

* * * * *